(12) United States Patent
Arbogast et al.

(10) Patent No.: US 7,162,322 B2
(45) Date of Patent: Jan. 9, 2007

(54) CUSTOM PROSTHETIC LINER MANUFACTURING SYSTEM AND METHOD

(75) Inventors: Robert E. Arbogast, Mt. Sterling, OH (US); James M. Colvin, Hilliard, OH (US); Christopher T. Kelley, Columbus, OH (US); Greg Pratt, Boca Raton, FL (US)

(73) Assignee: The Ohio Willow Wood Company, Mount Sterling, OH (US)

( * ) Notice: Subject to any disclaimer, the term of this patent is extended or adjusted under 35 U.S.C. 154(b) by 171 days.

(21) Appl. No.: 10/724,526

(22) Filed: Nov. 28, 2003

(65) Prior Publication Data

US 2005/0119777 A1 Jun. 2, 2005

(51) Int. Cl.
G06F 19/00 (2006.01)
A61F 2/78 (2006.01)
A61F 2/80 (2006.01)

(52) U.S. Cl. .................. 700/118; 700/98; 700/117; 700/182; 623/33; 623/36; 623/901

(58) Field of Classification Search .............. 700/95, 700/98, 117, 159, 182, 118; 623/33, 901, 623/16.11, 20.14, 20.18, 20.21, 23.15, 36; 705/2, 26; 600/587
See application file for complete search history.

(56) References Cited

U.S. PATENT DOCUMENTS

| | | | |
|---|---|---|---|
| 4,319,136 A | 3/1982 | Jinkins | 250/456 |
| 4,923,474 A | 5/1990 | Klasson et al. | 623/33 |
| 4,923,475 A | 5/1990 | Gosthnian et al. | 623/37 |
| 4,971,060 A | 11/1990 | Schneider et al. | 128/653 |
| 5,258,037 A | 11/1993 | Caspers | 623/36 |
| 5,295,483 A | 3/1994 | Nowacki et al. | 128/660 |
| 5,376,132 A | 12/1994 | Caspers | 623/36 |
| 5,603,122 A | 2/1997 | Kania | 2/239 |
| 5,781,652 A * | 7/1998 | Pratt | 623/901 |
| 5,830,237 A * | 11/1998 | Kania | 623/36 |
| 5,888,216 A * | 3/1999 | Haberman | 623/36 |
| 5,901,060 A * | 5/1999 | Schall et al. | 700/98 |

(Continued)

FOREIGN PATENT DOCUMENTS

WO   WO 03/003145 A2   1/2003

OTHER PUBLICATIONS http://www.owwco.com/HTML Viewer.asp?PK=whatist . . . , "What is Tracer?", 2 web pages, Aug. 15, 2003.

(Continued)

Primary Examiner—Leo Picard
Assistant Examiner—Charles Kasenge
(74) Attorney, Agent, or Firm—Standley Law Group LLP (57) ABSTRACT

A system and method for manufacturing a custom prosthetic liner. The system may include a shape capture device for capturing the shape of a residual limb. The captured shape may be used to generate a 3-dimensional electronic liner model using a processor and specialized software. A 3-dimensional electronic model of the residual limb may also be produced. Preferably, an interface is provided that allows a user of the system to alter the shape and/or size of the 3-dimensional model(s) to allow the subsequently-produced liner to accommodate particular features of the residual limb. Data associated with at least the resulting 3-dimensional liner model is provided to a manufacturing facility equipped to produce a custom liner therefrom. The data may be remotely transmitted to the manufacturing facility. A positive likeness of the residual limb is created from the data associated with the 3-dimensional model(s), and is subsequently used as a mold core in the liner molding process.

92 Claims, 3 Drawing Sheets

U.S. PATENT DOCUMENTS

| | | | |
|---|---|---|---|
| 5,911,126 A | 6/1999 | Massen | 702/153 |
| 5,954,647 A | 9/1999 | Bova et al. | 600/407 |
| 6,075,883 A | 6/2000 | Stern et al. | 382/144 |
| 6,125,197 A | 9/2000 | Mack et al. | 382/154 |
| 6,177,034 B1 | 1/2001 | Ferrone | 264/40.1 |
| 6,259,942 B1 | 7/2001 | Westermann et al. | 600/426 |
| 6,358,453 B1 | 3/2002 | Slemker et al. | 264/222 |
| 6,383,148 B1 * | 5/2002 | Pusch et al. | 600/587 |
| 6,406,499 B1 | 6/2002 | Kania | 623/36 |
| 6,463,351 B1 | 10/2002 | Clynch | 700/163 |
| 6,520,964 B1 * | 2/2003 | Tallarida et al. | 623/20.14 |
| 6,665,577 B1 * | 12/2003 | Onyshkevych et al. | 705/26 |
| 6,968,246 B1 * | 11/2005 | Watson et al. | 700/98 |
| 2002/0103545 A1 | 8/2002 | Arbogast et al. | 623/36 |
| 2003/0009354 A1 * | 1/2003 | Arbogast et al. | 705/2 |
| 2004/0243252 A1 | 12/2004 | Carstens | 623/34 |
| 2005/0216095 A1 | 9/2005 | Egilsson | 623/27 |

OTHER PUBLICATIONS http://tracercad.com/product.html, Tracer Cad Products, The Tracer Premier System, 1 web page, Aug. 15, 2003.
http://www.tracercad.com/t-ring.html., Tracer Cad Products, Omega T-Ring, 1 web page, Aug. 15, 2003.
http://www.tracercad.com/fabrication.html, Tracer Cad Fabrication, Tracer Central Fabs, 1 web page, Aug. 15, 2003.
http://www.tracercad.com/aboutus.html, Tracercad About Us, Why Omega, 1 web page, Aug. 15, 2003.
http://www.tracercad.com/perspective.html, Tracercad About Us, the O&P Perspective, 1 web page, Aug. 15, 2003.
Publication by Ohio Willow Wood entitled Perpetual Motion, 12 pages.

* cited by examiner

CUSTOM PROSTHETIC LINER MANUFACTURING SYSTEM AND METHOD

BACKGROUND AND SUMMARY OF THE INVENTION

The present invention relates to the production/manufacturing of custom liners for use with prosthetic limbs of various type. More specifically, the present invention relates to a system and method of manufacturing custom prosthetic liners, whereby a prosthetist or other qualified practitioner can capture the shape of an amputee's residual limb, manipulate data relating to said shape, if desired, and transmit or otherwise provide said data to a manufacturing facility that is equipped to receive the data and to manufacture a custom prosthetic liner therefrom.

While there are various types of prosthetic limbs, the most common are likely those designed to replace some portion of an arm or leg. While a liner manufactured by the system and method of the present invention will work equally well in either application, for purposes of simplicity, we will confine the immediately following discussion of the present invention and relevant known technologies primarily to that of a prosthetic leg. From this discussion, it can be understood that the system and method of the present invention offers advantages not available with known systems and methods for producing prosthetic liners—regardless of the specific type of liner produced.

Most prosthetic legs may be categorized as either below knee (BK), or above knee (AK) prosthetics. A BK prosthetic leg is designed to fit an amputee whose residual limb terminates at some point below the knee joint (i.e., the knee joint is still present). BK amputations are often referred to as transtibial amputations, as the amputation point passes through the tibia of the lower leg. An AK prosthetic leg is designed to fit an amputee whose residual limb terminates at some point above the knee joint (i.e., the knee joint has been removed). AK amputations are often referred to as transfemoral amputations, as the amputation point passes through the femur of the upper leg. Other categories of prosthetic legs include Symes, knee disarticulations, and hip disarticulations.

Whether a prosthetic leg is designed for a BK or an AK amputee, the leg will generally have some common components. For example, a BK prosthetic leg will generally have an upper portion comprising a socket that is provided to receive a portion of the amputee's residual limb. To the bottom of the socket is typically affixed a lower portion, normally comprising an upright assembly of some type that is connected to a foot or ground-contacting portion. During initial development of prosthetic legs, the upright assembly may simply have been a rod or similar structure used to impart the prosthetic leg with the proper length. A foot or similar structure may not even have been included. Modern BK prosthetic legs may make use of more complex upright assemblies that may provide for damping or other desirable properties. The upright assembly portion of a BK prosthetic leg may also be shaped to simulate the appearance of a real leg.

AK prosthetic legs will also generally have an upper, socket portion, that is provided to receive a portion of the amputee's residual limb. An AK prosthetic limb will also typically have a lower portion attached to the bottom of the socket. Normally, the lower portion of an AK prosthetic limb will also have an upright assembly of some type that is connected to a foot or ground-contacting portion. Older AK prosthetic limbs sometimes incorporated a rudimentary type of pivoting assembly to connect the lower portion to the socket. This allowed the amputee to swing the lower portion of the prosthetic limb forward during walking, in an attempt to simulate the amputee's natural gait. Modern AK prosthetic limbs are typically more complicated. For example, hydraulic or pneumatic cylinders, or some other type of damping device may be provided at the knee joint to better control the bending thereof.

Whether the prosthetic leg in question is of the BK or AK type, and whether the leg is simple or complex in design, acceptable use thereof still depends to a great extent on the fit of the amputee's residual leg into the socket of the prosthetic leg. No matter how well the prosthetic leg is otherwise designed, if the fit of the residual leg within the socket is not adequate, the prosthetic leg may irritate the residual leg, cause pain to the amputee, and/or may not be adequately retained. Thus, without a proper fit of the residual leg to the socket, a prosthetic leg can be substantially unusable.

In the early days of prosthetics development and manufacture, amputees had little choice as to how a prosthetic leg was fit and retained on the residual limb. For example, at one time, both BK and AK amputees had to rely on a "skin fit," whereby the skin of the residual leg produced a seal against the inner surface of the socket. In this retention method, at least a portion of the air in the socket is displaced by the residual leg during donning of the prosthetic leg. The displacement of air ideally creates a vacuum within the socket that retains the prosthetic leg on the residual leg. The seal between the skin and the inner surface of the socket is crucial to preventing air from entering the socket and, therefore, maintaining the vacuum.

There are numerous problems with a skin fit, however. Most notably, the constant contact of the skin against the hard inside surface of the socket can become painful, and can also cause problems with the skin of the residual leg. For example, the fit of the socket against the residual leg may press on nerves or other sensitive spots thereof. This problem may be exacerbated when the residual leg has little flesh, or exhibits particularly bony areas. Also, the skin of the residual leg may become irritated, chapped or raw, or may otherwise develop sore spots, lesions, or similar areas of weakness due to its contact with the socket. A skin fit may also cause the residual leg to perspire, jeopardizing the seal between the residual leg and socket, and further contributing to problems with the amputee's skin. Additionally, when employing a skin fit, powders, gels, or other similar lubricants are typically required to be spread over the residual leg and/or the inner surface of the socket in order to allow the residual leg to be properly inserted therein. Such surface modifiers are not only messy, they may be uncomfortable, and may further contribute to problems with the skin of the residual leg.

To alleviate the above-described problems, attempts have been made to produce a covering that may be placed over the residual leg prior to its insertion into the prosthetic leg socket. These attempts initially involved only BK prosthetics. The first such coverings developed for this purpose are best characterized as socks. These socks were typically manufactured of a fabric material of some thickness, which could be pulled over the distal end of the residual leg prior to its insertion into a socket. Such socks were problematic, however, particularly because they often lacked adequate comfort and secure suspension.

In an attempt to overcome the deficiencies of the sock-type liner, a silicone liner was introduced. This initial silicone liner was offered in the form of a kit. Before employing the kit to produce a liner, it was first necessary to produce a mold of the amputee's residual leg. This was typically accomplished by creating a cast of the residual leg, and then filling the cast with plaster or some other material to create a positive mold. The materials provided in the kit could then be mixed together in a lab, and somehow applied to the outer surface of the mold. As can be imagined, this process is cumbersome, messy, and likely produces a liner of substantially less than uniform thickness. The liner also could not simply be purchased from a supplier but, rather, had to be produced by a prosthetist or other practitioner qualified to cast the residual leg and subsequently produce the liner. In addition, a liner produced using this kit was required to be attached to a prosthetic leg via a pin connection, as a suction fit between the liner and the socket was not attainable. Moreover, as silicone tends to cling to other materials, a lubricant was again typically required to allow its insertion into a prosthetic leg socket.

A generic silicone liner was next developed, which liner dispensed with the necessity of purchasing a kit of materials and handcrafting a liner therefrom. This liner consisted substantially of a roll-on silicone sleeve. A few different sizes of the sleeve were produced, and the practitioner was required to select the size which most closely approximated the size of the amputee's residual leg. This generic silicone sleeve was designed primarily to allow for improved suspension (retention) of a prosthetic leg on a residual leg via a mechanical pin lock. Unfortunately, because the residual leg can be of virtually unlimited size and shape, it was often difficult to select a liner that fit acceptably. Additionally, similar to its predecessor, this liner required that powder be applied to the residual leg, to the outer surface of the liner, or both, in order to facilitate donning of the liner and insertion thereof into a prosthetic leg socket.

Next introduced was what may be accurately described as a gel sock. As opposed to the silicone material of two of the aforementioned liners, this gel sock was manufactured by dipping a former into a gel material. The gel sock was very thin and offered no means of suspension. The thin construction also provided for little cushioning. Another substantial disadvantage of the gel sock was that it commonly caused adverse reactions of an amputee's skin when worn. This is believed to be the result of the gel material itself, which is thought to have been solvent-based.

A urethane liner was subsequently introduced, which liner alleviated some of the problems inherent to the above-described liners. Unfortunately, this urethane liner had problems of its own. First, a prosthetist was again required to make a cast or mold of an amputee's residual leg, which cast or mold had to be thereafter sent to the sole company that produced the liners. Because the manufacturing process associated with this liner is relatively slow, it often took weeks to receive the liner after sending out the cast or mold. These urethane liners were generally also substantially thicker than the liners previously described. Because the urethane material has a much higher density, these liners were also typically much heavier than the preceding liners. A further drawback associated with this liner and liner manufacturing method is the fact that the liner manufacturer must keep a positive mold of the amputee's residual leg if additional liners are to be made for that amputee in the future. As the typical mold was made from plaster, such molds are generally, fragile, and take up a not insubstantial amount of space. Yet another drawback was that this system was not compatible with a pin suspension. Additionally, similar to several of the aforementioned previously known liners, the amputee's residual leg generally had to be lubricated prior to donning the urethane liner.

It should be realized, that in addition to the illustrated deficiencies inherent to the aforementioned previously known liners, such liners were also typically only available for use with BK prosthetics. In fact, to the best of the Applicant's knowledge, no form of liner was available for use with AK prosthetics until approximately the mid-1990's, and the use of liners with AK prostheses employing suction retention did not gain acceptance until approximately 2001.

The Applicant currently manufactures and sells a liner that is substantially superior to those liners discussed above. The Applicant's current liner, known commercially as the Alpha® liner, is available to amputees as an off-the-shelf product. This liner is generally manufactured from a novel block copolymer material to which is adhered a fabric covering. The fabric-covered liner is easily rolled onto the residual leg or arm, with the fabric material facing out. The fabric material allows for easy donning and doffing of a prosthetic limb, as the inner surface of the prosthetic limb socket slides easily over the fabric. The fabric material also improves the durability, stability, and cosmetic appearance of the liner. In comparison to the aforementioned liners, the Applicant's existing liner is generally longer, with the block copolymer material typically extending substantially to the edge of the fabric that typically extends beyond the brim of the socket. The design of the Applicant's existing liner offers superior cushioning, better prevents air entry, and reduces the chances of perspiration forming around the portion of the residual limb that resides within the prosthetic limb socket. Also, the particular block copolymer material used allows the liner to better conform to the shape of the amputee's residual limb, and may contain additives, such as mineral oil, which act to condition the skin.

In a similar manner to the aforementioned and previously known liners, however, the Applicant's present liner has been heretofore available in only a few standard sizes. Thus, an amputee has up until now been required to order an Alpha® liner of a size that most closely approximates the size of their residual limb. Due to its design and construction, such an off-the-shelf Alphas liner still typically provides for a comfortable fit—and is still generally superior to previous liners. This is due in part to the ability of the Alpha® liner to conform to the shape of an amputee's residual limb as the liner is worn. However, the ability to manufacture such a liner that is also customized to fit an individual amputee remains desirable, as such a custom liner would provide for an even further improvement in fit, and may be especially beneficial to amputees who have, for example, highly sensitive, bony, or unusually shaped residual limbs.

For certain of the reasons described above with respect to known prosthetic liners, as well as for other reasons, it has up until now been impractical to produce a custom liner. For example, using typical known techniques would require the plaster casting of an amputee's residual limb, the production therefrom of a positive replica of the residual limb, and storage of the positive replica to allow for the production of future liners. In addition, it would be extremely cost prohibitive to manufacture a liner mold designed specifically to account for the peculiarities of each amputee's residual limb.

The system and method of the present invention overcomes the aforementioned problems and allows the manufacture of a custom prosthetic liner of any type (i.e., leg, arm, etc.) in a timely and cost efficient manner. The system and method of the present invention eliminates the need to cast an amputee's residual limb in order to obtain the accurate shape thereof. Rather, one embodiment of the system and method of the present invention can obtain the accurate shape of an amputee's residual limb by making use of a shape capture device to capture the 3-dimensional shape of the residual limb with a high degree of accuracy, or through the application of measurements to a shape template. Software associated with the shape capture device may optionally be used to convert the 3-dimensional shape (image) into a 3-dimensional electronic model that accurately represents the residual limb. Alternatively, the software associated with the shape capture, or other software, can apply measurements to a shape template to produce a 3-dimensional electronic model that represents the residual limb. The software, through an interface, preferably also allows a prosthetist or other qualified practitioner to produce a 3-dimensional electronic model of a liner that makes use of the exterior shape of the residual limb to calculate its interior geometry. The liner model can be generated regardless of whether a residual limb model has been generated. If used, the practitioner can modify the residual limb model in order to further fine-tune the fit of the liner that will be produced therefrom. Once the liner model is deemed to be in acceptable form, the data associated therewith is transmitted or otherwise provided to a manufacturing facility that is equipped to receive the data and to produce a liner therefrom. In one embodiment of the present invention, the data is used to produce a 3-dimensional positive likeness of the (modified or unmodified) residual limb from a selected material. The 3-dimensional positive likeness of the residual limb can then be used as a mold core in conjunction with a standard (existing) liner mold cavity to produce a custom prosthetic liner. Thus, this embodiment of the system and method of the present invention does not require the use of a wholly unique liner mold in order to produce the custom liner. In another embodiment of the present invention, the data may be used to produce unique positive (core) and negative (cavity) portions of a liner mold. In this embodiment of the present invention, the whole of each mold is then unique to a particular amputee. While this method is likely more costly than the previously described method, it is contemplated that such molds could be manufactured of low cost materials, as such molds are not likely to experience a high number of molding cycles.

The system and method of the present invention may be utilized by having an amputee visit, for example, a prosthetist or other practitioner's office, wherein the shape capture of the amputee's residual limb and the optional modification of the subsequently generated electronic model may take place. Alternatively, the shape capture device may be transported to the location of the amputee. In this case, the captured shape of the residual limb can be converted to a 3-dimensional model and optionally modified while at the amputee's location, such as through the use of a laptop, pen, or pocket computer, or a personal data assistant (PDA), or the captured shape of the residual limb may be saved for later processing at a different location. The finalized data representing the electronically modelled residual limb can be delivered to a qualified manufacturing facility in any number of ways, such as, for example, by delivery on a machine readable storage medium, by wired or wireless transmission over the Internet, or by direct transfer from machine to machine (such as, for example, from a laptop computer to another computer, or to a CNC or similarly controlled machining device). In an alternate embodiment of the present invention, a conventional plaster cast of the residual limb can be taken, and the cast subsequently digitized to obtain an electronic model of the residual limb. This embodiment of the present invention may be practiced, for example, when a cast of the residual limb already exists, or when a practitioner prefers to continue working with plaster.

In any event, the system and method of the present invention allows an amputee to easily acquire a prosthetic liner that is customized to fit his/her residual limb, thereby providing for maximum comfort and support. Further, the first and subsequent custom liners can be ordered from the manufacturer(s) in the same manner as other prosthetic supplies, and can be delivered to the amputee in a timely manner and at a reasonable price. The system and method of the present invention also makes the storage of residual limb casts or molds optional, as the data required to produce the liner can be stored in electronic form. The system and method of the present invention may further permit a prosthetist or other qualified practitioner to specify options for inclusion on the liner, such as, for example: different types of suspension components and their size, location and orientation; bladders (including inflatable bladders) and their location and size; liner materials and material properties, including hardness, elasticity; the inclusion of additives, such as anti-microbials, therein; liner cover properties; and, sensors and their type and location. Additionally, the system and method of the present invention may allow for the manufacture of a custom liner that permits an amputee whose residual limb size/shape has changed, to continue using his/her existing socket. Similarly, it may be possible to produce custom liners that allow amputees to use a generic socket, with the difference in shape being accounted for by the liner, thereby greatly reducing the overall cost of a prosthetic limb. Therefore, as can be seen from the foregoing discussion, and as can be even better understood from a reading of the following detailed description of exemplary embodiments, the system and method of the present invention permits the practical manufacture of a custom prosthetic liner that has not been heretofore possible.

Although, for reasons of clarity, the preceding discussion has been directed primarily to the use of liners with prosthetic legs, it should be understood that the system and method of the present invention can be used to produce a prosthetic liner for virtually any type of prosthesis. Additionally, while in one preferred embodiment the system and method of the present invention is used to produce a custom prosthetic liner having a construction like that of the Applicant's current Alpha® liner, nothing herein is meant to limit the use of the system and method of the present invention to such a construction or to any particular liner materials.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF THE EXEMPLARY EMBODIMENT(S)

The system and method of the present invention allows for the efficient and cost effective manufacturing of a custom prosthetic liner. The system and method of the present invention will generally include: a means for scanning, photographing, digitizing, measuring, or otherwise capturing the 3-dimensional shape of an amputee's residual limb; an optional means for converting the captured shape of the residual limb into a viewable 3-dimensional model; a means for producing a viewable 3-dimensional liner model; a means for manipulating the 3-dimensional residual limb and/or liner model in order to further enhance and customize the fit and performance of the liner that will be manufactured therefrom; a means for providing the finalized data associated with the 3-dimensional liner model to a facility that will manufacture a liner from the data; a means for producing a 3-dimensional likeness (positive) of the (modified or unmodified) residual limb from the data; and a means of using the 3-dimensional positive with either existing or unique molding components to produce a liner customized to fit the amputee's residual limb. As will become more clear hereafter, certain embodiments of the present invention may not include particular ones of these components, or may include additional components.

It is to be understood that the system and method of the present invention can be used to produce a custom liner to fit virtually any type, size, or shape of prosthetic limb. While the above discussion with respect to the present invention and known prosthetic liners focused primarily on a liner for a prosthetic leg, the system and method of the present invention is also capable of producing liners for other types of prostheses, such as, for example, prosthetic arms.

Manufacture of a custom prosthetic liner according to one embodiment of the present invention requires an accurate determination of the shape of the amputee's residual limb. The residual limb may be scanned, photographed, videotaped, digitized, or otherwise subjected to any process that can be reasonably employed to accurately capture its shape. For example, the shape of the residual limb may be captured by using a digitizing pen to trace over its surface. Preferably, however, the residual limb is exposed to a multiple-image detector shape capture device that is able to accurately, and substantially instantaneously, capture the 3-dimensional shape of the residual limb. An exemplary, and particularly suitable multiple-image detector shape capture device and its method of use is disclosed in U.S. patent application Ser. No. 10/641,895, entitled A Medical Socket Contour Scanning System, which is hereby incorporated by reference herein. As can be understood from reference to U.S. patent application Ser. No. 10/641,895, the shape of the amputee's residual limb can be accurately and substantially instantaneously captured by using a series of spaced-apart image detectors that are mounted to a framework and are disposed to substantially surround the residual limb.

Once the shape of the residual limb has been captured, it may be converted into a viewable 3-dimensional model by software in electronic communication with a processor. Thus, from the captured shape, a 3-dimensional electronic model can be rendered, which the prosthetist or other user of the system is preferably able to observe from all angles. The software also preferably allows a user of the system to rotate, flip, mirror, and otherwise alter the viewing angle of the model in order to adequately inspect and/or observe the shape of the residual limb. Alternatively, no viewable model of the residual limb may be generated. Rather, the numeric data associated with the captured shape of the residual limb may simply be used to help produce an electronic liner model. As discussed in more detail below, the software employed in the present invention is preferably also provided with an interface or is otherwise adapted to allow the user of the system to modify the 3-dimensional residual limb and liner models as deemed necessary to account for particular features of the residual limb or particular preferences or problems of the amputee. For example, in order to account for areas of the residual limb that may be especially sensitive, the model(s) may be manipulated to produce a liner that is thicker in certain areas than in others.

Figure 1:
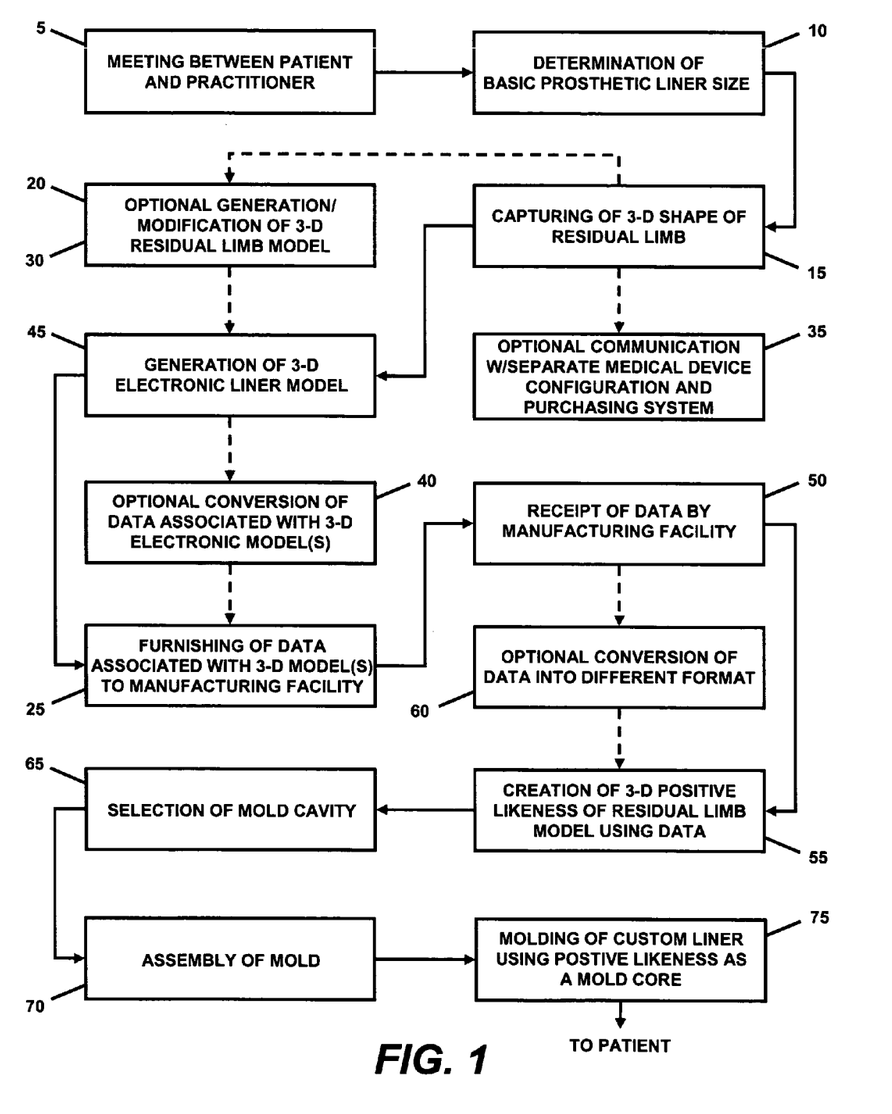
FIG. 1 is a diagrammatic representation of the use of one embodiment of the system and method of the present invention, whereby a custom liner is produced for an individual amputee.

As mentioned previously, in an exemplary embodiment of the present invention, the shape capture portion of the liner manufacturing process may be accomplished in a prosthetist or other practitioner's office, or at the location of the amputee. Consequently, the first substantive step of manufacturing a custom liner according to the present invention involves a meeting between the patient (amputee) and a practitioner 5. According to the system and method of the present invention, the amputee may visit the practitioner, or the practitioner may visit the amputee. During the visit, the practitioner will typically examine the residual limb, and may make note of particular characteristics of the residual limb that will require special attention during the liner design process. The practitioner next determines an appropriate basic liner size 10, which is typically selected based on the relative size of the residual limb. Thereafter, an acceptable shape capture system is employed to capture the 3-dimensional shape of the amputee's residual limb 15. For example, when the multiple-image detector shape capture device described in U.S. patent application Ser. No. 10/641,895 is employed, a special pattern imposer is typically placed over the residual limb and the shape capture device is properly oriented thereto. The pattern imposer may be of various thickness, depending largely on the anatomy and physiology of the residual limb to be scanned, and the medical device to be constructed from the scanned data. The use of pattern imposers of different thickness is explained in detail in a U.S. continuation-in-part patent application filed in the name of Greg Pratt on Oct. 7, 2003, and entitled A Medical Socket Contour Scanning System, which application is hereby incorporated by reference herein. The pattern imposer may be further landmarked by the practitioner to indicate areas on the residual limb of particular interest. These landmarks will allow such areas to be more easily located on the subsequently generated electronic model(s). The multiple-image detector shape capture device, or other shape capture device, is commonly connected to a laptop computer that is loaded with the design software that determines the numeric data defining the shape of the residual limb, optionally, allows for the conversion of the captured residual limb shape into a 3-dimensional electronic model 20 thereof, and allows for the generation of a 3-dimensional electronic liner model 45. Other processing devices may also be used for this purpose, such as, for example, a desktop computer, a pen computer, a pocket personal computer (pocket PC), or a personal data assistant (PDA). Alternatively, it is also contemplated that the captured image could simply be converted into numerical data by a processor that is integrated into the shape capture device and thereafter stored on an acceptable storage medium for later conversion into a 3-dimensional model. In any event, once the practitioner is satisfied that the shape capture procedure was properly completed, the next step of the process may be embarked upon.

Assuming that the captured shape of the residual limb has been acceptably converted into numeric data, the practitioner need not necessarily do any more than subsequently furnish the data associated therewith to the liner manufacturer 25. In such a case, the interior of the liner will be made to conform to the captured shape of the residual limb and will be of some default, and substantially uniform, thickness. However, most likely, the practitioner will want to modify the model 30 to account for nuances of the particular residual limb in question and/or of the particular prosthetic socket with which the liner will be worn. Hence, a 3-dimensional electronic model of the residual limb will typically be generated 20 to allow the practitioner (or other qualified user of the system) to view the shape of the residual limb and make changes thereto 30. For example, the practitioner may desire an overall general thickness for the liner, which may correspond to, for example, a global reduction in the size of the residual limb model. Other modifications to the shape of the residual limb model 30 may also be made, such as, without limitation, those to account for particular scarring of the residual limb, those to provide additional liner material around protrusions or bony areas of the residual limb, and those to provide areas of relief around particular other features of the residual limb. When the liner will be worn by a BK amputee, the practitioner may also manipulate the model in the area of the patella tendon to ensure that the knee is properly supported but allowed to flex adequately.

The software allows the data associated with the captured shape of the residual limb to be used in producing a 3-dimensional electronic liner model 45. The data may be unmodified, or may be modified by a practitioner, as described above. Either way, the residual limb model (if generated) is used to help define the interior geometry of the liner. If no residual limb model is generated, the captured residual limb shape data may be used directly in the generation of the liner model. From such data, a 3-dimensional electronic liner model may be generated 45. As stated above, the practitioner can specify an overall liner thickness. Distal end liner thickness may be separately specified, such as to provide extra cushioning to the often sensitive distal end of the residual limb. Similarly, posterior liner thickness may be altered over a user specified region to allow for a more unencumbered and comfortable bending of the knee, or to provide hamstring relief. Likewise, liner thickness may be altered in other areas, such as to provide extra cushioning along the anterior portion of the residual limb. In one embodiment of the present invention, the software also permits the practitioner to select options and features of the liner. For example, the practitioner may specify for inclusion in/on the liner, options or properties such as: different types of suspension components and their size, location and orientation; bladders (including inflatable bladders) and their location and size; liner materials and material properties, including hardness, elasticity; the inclusion of additives, such as anti-microbials, in the liner material; liner cover properties; and, sensors and their type and location. Liner material options can include, without limitation, polymer materials such as silicone, urethane, thermoplastic elastomers (especially styrenic block copolymers), or combinations thereof. Once the practitioner has selected all the desired parameters, a final 3-dimensional electronic liner model is preferably generated and made available for viewing 45.

In addition to the optional modification 30, 45 of the 3-dimensional model(s), it is also contemplated that the system and method of the present invention may be used in conjunction with an automated medical device configuration and purchasing system 35. Such a system, its method of use, and a computer program for operating the system, are disclosed in U.S. patent application Ser. No. 09/893,535, entitled *System, Method, And Computer Program Product For Configuring And Purchasing A Medical Device*, which is hereby incorporated by reference herein. U.S. patent application Ser. No. 09/893,535 teaches a system and method that allows a prosthetist to substantially automatically configure one or more medical devices based on inputted patient information. The system is able to configure multiple embodiments of an acceptable device, such as, for example, a "good," "better," and "best" alternative, or the lightest or least expensive alternative. Thus, in conjunction with ordering a custom liner, the system and method of the present invention may also allow for the simultaneous configuration and/or ordering of other prosthetic components or a complete prosthetic device. For example, a prosthetic device for use with the custom liner may be ordered at the same time as the custom liner. The software (program) associated with the medical device configuration and purchasing system may separately reside on the processing device used in the shape capture process, or may be accessible via connection to a server or over the Internet. In one exemplary embodiment of the present invention, an interface or some other means of communication between the two programs and systems is provided, so that data may be shared and used between/by both systems.

Once the practitioner is satisfied with the residual limb model and/or the liner model, the data associated therewith must be furnished to a manufacturing facility 25 that is equipped to receive the data and to produce a liner therefrom. In addition, in one embodiment of the present invention, it is possible that prior to transmission to the manufacturing facility, the data may be optionally converted 40 by the modelling software associated with the shape capture system, or by associated software, into a format that can be directly used by a computer-controlled machining center, or another similar device. It is contemplated that the data, in whatever format, may be furnished to the manufacturing facility 25 in virtually any manner. Obviously, the data could be delivered in person by the practitioner, or some other person acting on behalf of the practitioner. In such case, it should be understood that the data may be stored and provided on virtually any machine readable medium, including, but not limited to, a floppy disk, a compact disc or other optical medium, a magneto-optical disk, a magnetic tape, a PROM or similar other magnetic chip, a punch card, or a paper tape. It is only required that the manufacturing facility is able to read the data from the particular medium, or have the data transferred from the particular medium employed to a medium readable by the facility.

Alternatively, the data associated with the residual limb model and/or the liner model can be provided to the manufacturing facility remotely. For example, the software may store the data in the temporary memory of a desktop computer, laptop computer, pen computer, pocket personal computer (pocket PC), or PDA, or on a readable/writable storage medium associated with any thereof. At some point thereafter, the practitioner can transmit the data to the facility via any number of means, including, but not limited to, by wired or wireless transmission over the Internet, or by direct transfer from machine to machine (such as, for example, from a laptop computer to another computer, or to a CNC or similarly controlled machining device). Therefore, it should be understood that the device used to remotely transfer the data to the manufacturing facility may be equipped with any number of data transmission components, such as, for example, a dial-up modem, a DSL or ISDN modem, a cable modem, a WiFi card, a Bluetooth® card, a WCDMA card, a network interface card (NIC), or a wireless networking card. In yet another embodiment of the present invention, it is possible that an amputee may visit a manufacturing facility that employs its own qualified practitioner, or allows for its use by outside practitioners. In this case, it is possible that once collected/generated, the data associated with the residual limb/liner model may be transferred from one computer, server, database or other storage means to another similar or different storage means of the facility via a wired connection, or by using any of the aforementioned transmission means and devices to transmit the data over, for example, a local area network (LAN) or wireless local area network (WLAN). Via any of the aforementioned data transfer means, it is also possible for the facility to provide the data to another similar facility, or to virtually any other entity that is involved with the liner manufacturing process or that otherwise has a need for the information.

In an embodiment of the present invention alternative to that described above, a more rudimentary and conventional method may be used to capture the shape of an amputee's residual limb. For example, if a practitioner does not have access to an electronic shape capture system, the shape of the residual limb could still be captured via a more conventional method, such as plaster casting or tape measurement. The plaster cast or the measurements could then be converted to an electronic model of the residual limb by the practitioner, another practitioner, or the manufacturer. For example, the plaster cast could be provided to the manufacturer for electronic shape capture. The electronic liner model can then be designed from an electronic model of the residual limb generated from the subsequent electronic shape capture process, or from the residual limb measurements. Also, the practitioner could design the liner directly without capturing or creating a model of the shape of the residual limb. For instance, a generic liner shape could be selected from an electronic library of initial liner shapes based on some minimal shape data associated with the amputee's residual limb (e.g., a few circumference and length measurements). The electronic generic liner shape could then be modified to form a custom liner shape. While this method would not generally be as accurate as designing the liner from a model of the residual limb, it may be an acceptable approach if, for instance, a small modification of an amputee's already existing liner is all that is required.

Once the data is received by the manufacturing facility 50, it can be used to initiate the liner manufacturing process. In an exemplary embodiment of the present invention, the data is used by a machining or carving device, such as, for example, a CNC machining device, to produce a 3-dimensional positive likeness 55 that corresponds in size and shape to the computer generated and, optionally, user-modified 3-dimensional electronic model of the residual limb. The data may be modified at the manufacturing facility 60 prior to being provided to the machining or carving device. The 3-dimensional positive likeness will serve as the custom mold core in the subsequent liner molding process. Any number of acceptable machining devices are available for this purpose and, although machining devices designed specifically for the prosthetics industry exist, the use of such is not required. It is also contemplated that other devices and methods commonly employed to produce 3-dimensional models may also be used to create the positive likeness. As previously mentioned, the data may have been converted 40 into a form acceptable to the particular machining device to be used prior to being furnished to the manufacturing facility. However, if data conversion is necessary, it is also possible that conversion is accomplished by software associated with the machining device itself or by some intermediary software or other electronic conversion means, after the data is received by the manufacturing facility 60. The 3-dimensional positive likeness/mold core may be produced from a number of materials. Preferably, however, the 3-dimensional positive likeness/mold core is produced from a material that is inexpensive, that is lightweight, that can be quickly machined or otherwise shaped, and that is of sufficient strength and durability to withstand the molding process. In one particular embodiment of the present invention, the 3-dimensional positive likeness/mold core is machined from a closed-cell foam material.

Once the custom mold core has been produced, a mold cavity is selected 65 for use therewith in the subsequent liner molding process. In one exemplary embodiment of the present invention, the custom mold core is used in conjunction with an existing, or common, mold cavity, to produce the liner. For example, a mold cavity used to produce Applicant's generic Alpha® liners described above, may be used in cooperation with the custom mold core to produce a custom prosthetic liner. In such a case, the mold cavity is selected based only on its size. That is, a mold cavity is selected that best corresponds to the size of the custom mold core and/or the custom liner to be produced. For example, there may be several generic mold cavities corresponding to various sizes of off-the-shelf liners. The custom mold core is assembled to the mold cavity 70, and the liner material is subsequently molded therebetween to form the custom liner 75. In this manner, the inside surface of the custom liner is imparted with the particular characteristics of the residual limb that are embodied in the custom mold core, while the outside of the custom liner is simultaneously provided with a substantially uniform and smooth surface for easy fitting into a prosthetic socket.

In another embodiment of the system and method of the present invention, a custom mold cavity can be used with an existing, or common, mold core. In yet a different embodiment, both a custom mold core and a custom mold cavity can be manufactured. The same data used to manufacture the custom mold core (based on the 3-dimensional likeness of the residual limb) can be used to manufacture the custom mold cavity. For example, the model defined by the data can be expanded to manufacture a mold cavity of an appropriate size to produce a liner of desired thickness when used in conjunction with a common (or existing) or custom mold core. While these alternative embodiments of liner manufacture would likely be more costly than the embodiment that uses a generic, or common, mold cavity, it is understood that the cost can be at least somewhat reduced by manufacturing the custom mold core and/or cavity from a low-cost material. For example, as the custom mold cavity likely will not be used to produce a significant number of liners, a softer, less wear-resistant, and easier to machine material than would typically be used may be employed therefor.

Once the custom liner(s) is produced, it may be picked up or delivered to the patient or to a practitioner. For example, if the custom liner is new to the patient, it may be preferable that the liner be initially provided to a practitioner to ensure that the fit to the residual limb and prosthetic socket is adequate. If a prosthetic device was ordered along with the liner, such as through the automatic configuration and purchasing system described above, both products can be simultaneously provided to the patient or practitioner. In such a case, it may be possible for the liner manufacturer to check the fit of the liner to the prosthetic socket prior to delivery—assuming, of course, that the liner manufacturer also manufactures or assembles the prosthetic device (or at least the socket portion thereof), or otherwise obtains the prosthetic device before providing the amputee with the custom liner.

Once the liner(s) is produced, the data associated therewith is preferably stored for later use should, for example, the amputee or practitioner wish to order an additional liner(s). The data may be stored in a variety of ways, including, for example, on any of the computer readable medium described above, on a computer hard disk, or in a server database. Preferably, the liner data is saved along with patient identifying information, thereby allowing for quick location of, and access to, the liner data, should another liner need to be made. In one embodiment of the system and method of the present invention, the liner data and patient information may be saved to the central database described in U.S. patent application Ser. No. 09/893,535. In this case, the liner data and patient information may thereafter be accessed as described in U.S. patent application Ser. No. 09/893,535 with respect to the patient-specific information used to configure and purchase a medical device. The liner data may be stored in one or more forms. For example, the liner data may be stored in a form used by the liner modelling software, and/or in a form that is used by a computer-controlled machining tool.

If the storage space is available, it is preferred that the custom mold core be saved for possible later use. As the custom mold core will generally be of very light weight and relatively compact size, an inordinate amount of storage space should not be required. Preferably, the custom mold core is stored in a manner that allows for easy identification and quick retrieval. For example, storage location data may be saved along with the liner and/or patient data. This permits for a quicker turnaround of a previously-produced liner upon receipt of a new order. It is contemplated that a storage and retrieval system for storing and working with existing custom mold cores may be operated manually, or may be an automated system. For example, in the former embodiment, a worker may simply retrieve a mold core from a specified location, by any commonly used means. In the latter embodiment, an automated mold core retrieval system may employed, whereby a mold core retrieval device can automatically retrieve a desired mold core based on storage information received from a data storage location. Usable automated storage and retrieval systems are well known, and need not be described in detail here. Storage and retrieval of a custom mold core may be automatically accomplished as a result of a signal generated by the system of the present invention upon completion of a liner order, or upon receipt of a new liner order. When a custom mold cavity is also manufactured, it may be stored in the same manner as the custom mold core. Alternatively, of course, the custom mold core may be destroyed after the initial liner order is completed. In this case, a new mold core must be produced from the respective stored data should another liner be ordered by the patient or a practitioner.

In another embodiment of the system and method of the present invention, it is possible to produce a custom liner that allows an amputee to continue using a prosthetic device even after a change in the shape and/or size of the amputee's residual limb negatively affects its fit with the prosthetic socket of the device. This is a well known problem in the field of prosthetics, and changes in the shape of a residual limb are not uncommon—especially over a short term period following the initial amputation. As discussed above, the fit of the residual limb to the prosthetic socket of a prosthetic limb is critical to the comfort of the amputee and to the proper use of the prosthetic limb. Thus, prosthetic sockets are custom-constructed to fit the residual limb of an individual amputee. However, if the shape and/or size of the residual limb changes at some point after the initial construction and fitting of the prosthetic socket, the prosthetic limb may become unusable, or at the very least, uncomfortable. Typically, the residual limb will shrink over time, particularly for some period after the initial amputation. Consequently, the prosthetic socket will often become loose on the residual limb, thereby causing inadequate retention of the residual limb, and possible discomfort to the amputee. If the change in the shape and/or size of the residual limb is significant enough, the amputee may no longer be able to wear the prosthetic limb as constructed, and a new prosthetic socket will have to be made and installed thereto. This can be both a time consuming and costly process, as a custom prosthetic socket can be one of the most costly individual components of a prosthetic limb.

Figure 2:
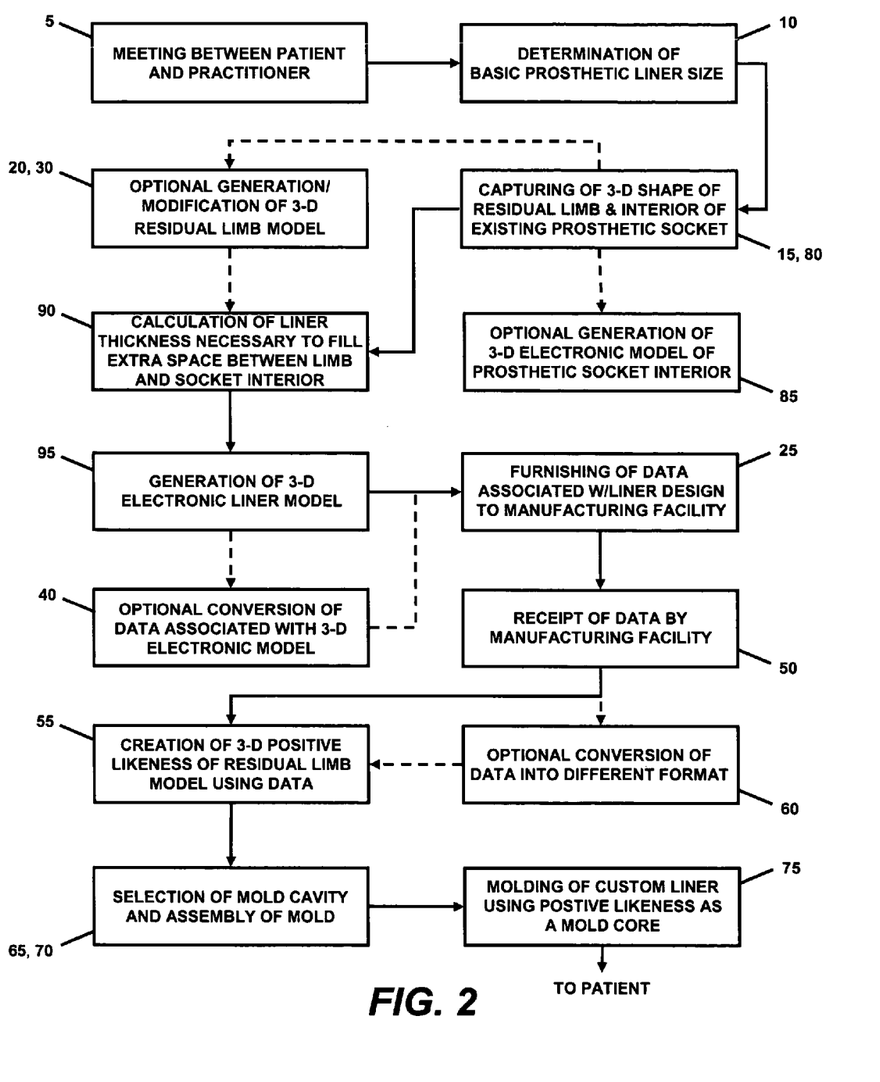
FIG. 2 is a diagrammatic representation of the use of an alternate embodiment of the system and method of the present invention, whereby a custom liner is produced that allows an individual amputee having a residual limb that has changed in shape and/or size to continue using his/her existing prosthetic socket.

The system and method of the present invention can be used to allow an amputee with a residual limb of changed shape and/or size to continue using his/her existing prosthetic socket. In this process, 3-dimensional images of the current shape of the residual limb are captured 15 by any of the means described above. In addition, however, the interior of the amputee's current prosthetic socket is also scanned or otherwise digitized 80 to obtain its 3-dimensional shape. This can be accomplished by using any of the aforementioned techniques. As also described previously, a 3-dimensional model of the residual limb may be produced from the captured shape 20 and, as previously described, may be modified by a user of the system 30. In addition, a 3-dimensional model of the prosthetic socket interior may be optionally generated 85 for viewing or, alternatively, the data corresponding to the prosthetic socket interior can simply be used (without generation of a viewable model) by the liner modelling software to determine the difference in size between the surface of the residual limb and the interior of the prosthetic socket. In this manner, the thickness of the subsequently-produced custom liner can be automatically calculated 90 and specified by the modelling software to account for the excess space between the residual limb and the prosthetic socket interior. The practitioner is preferably still able to make modifications to the 3-dimensional model of the residual limb, if optionally generated, in order to adjust the resulting liner—as the modelling software is able to determine the difference between the modified model and the interior of the prosthetic socket. Consequently, the interior of the resulting liner will be customized to accommodate the particular features of the amputee's residual limb, as described above, while the thickness of the liner will account for the space that now exists between the interior of the prosthetic socket and the surface of the residual limb. Once the liner thickness is calculated, a 3-dimensional electronic model of the liner is preferably displayed for viewing by the user of the system 95. As in the aforementioned embodiment, the user may be able to specify liner parameters and select options and/or accessories to be installed to/in the liner. As described in more detail above, the liner data is then sent to a manufacturing facility 25 for use in molding the custom prosthetic liner 75. Therefore, a custom liner can be efficiently and cost-effectively produced by this embodiment of the system and method of the present invention, which liner will allow the amputee to continue wearing his/her prosthetic limb even after a change in the shape and/or size of the amputee's residual limb.

In yet another embodiment of the system and method of the present invention, it is possible to produce a custom liner that will permit an amputee to wear a prosthetic limb having a generic prosthetic socket (i.e., a socket with a generic interior shape). The system and method employed in this embodiment is largely the same as described above. However, in this embodiment, a generic socket is also selected and a custom prosthetic liner is designed to allow the residual limb of the amputee to fit properly therein. It is contemplated that a series of generic prosthetic sockets can be provided, from which the most appropriate socket can be selected. Each of the series of generic sockets would differ primarily only in size, as is required to accommodate residual limbs of various size.

The system and method of the present invention can be used to capture the interior shape of each generic socket, as described above. Alternatively, the interior shape of the generic socket may be known from data developed/used in the manufacturing thereof. Thus, in a similar manner to the aforementioned process of producing a custom liner that allows an amputee with a residual limb of changed shape and/or size to continue using an existing prosthetic socket, a custom liner may be produced with an interior configuration customized to fit the residual limb of an individual amputee and an exterior designed to fit properly within a preselected generic prosthetic socket.

Figure 3:
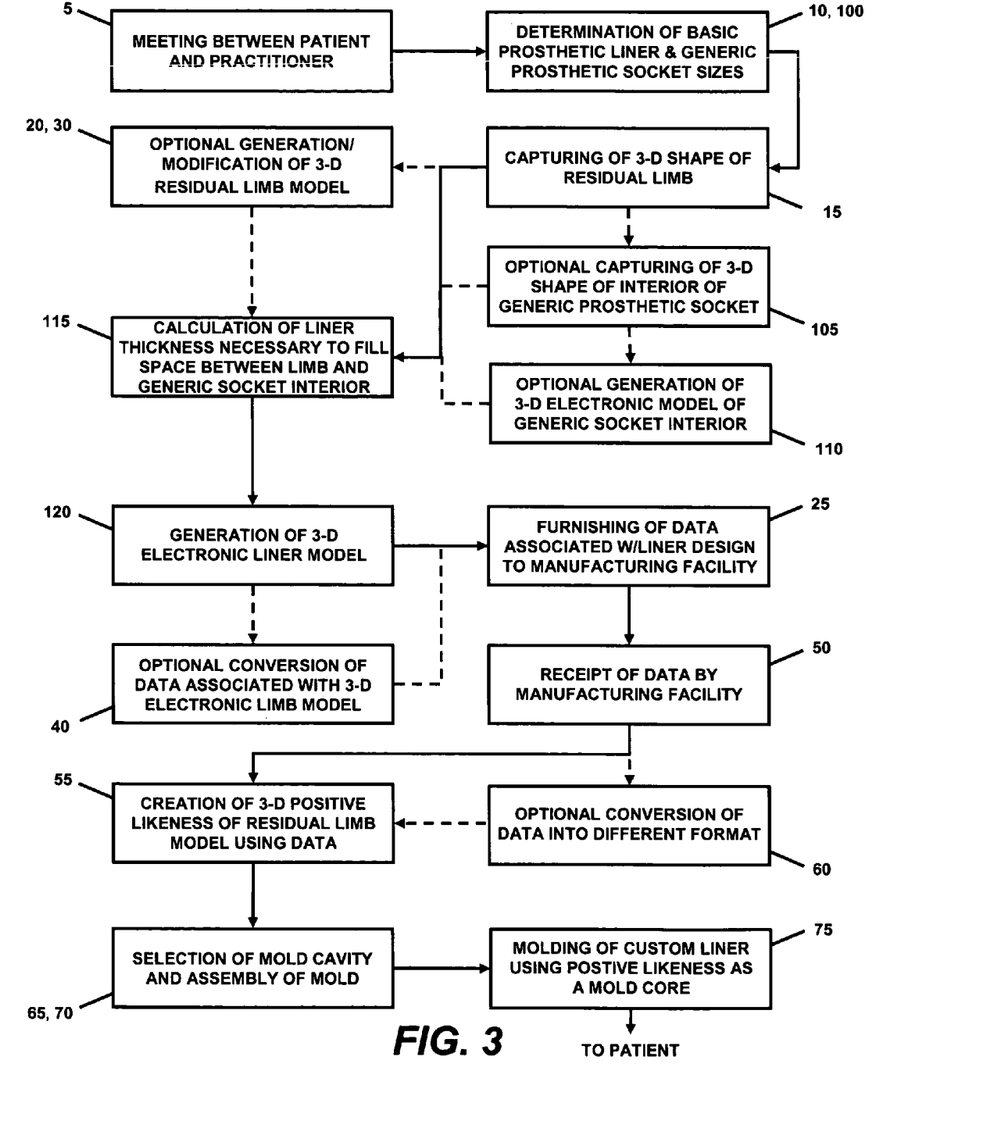
FIG. 3 is a diagrammatic representation of the use of another embodiment of the system and method of the present invention, whereby a liner is produced that allows for the custom fit of an individual amputee's residual limb to a generic prosthetic socket.

This particular embodiment of the present invention is accomplished, in conjunction with other already-described aspects of the system and method of the present invention, by having a practitioner initially select the one of a series of generic sockets that is most appropriately sized to generally fit the amputee's residual limb 100. The 3-dimensional shape of the amputee's residual limb is captured 15 and a 3-dimensional model may be optionally produced therefrom 20—by any of the techniques previously described. In this embodiment of the present invention, it is also necessary to know the 3-dimensional shape of the interior of the generic prosthetic socket. Thus, in one version of this embodiment, the interior of the generic prosthetic socket is also scanned, digitized 105 or otherwise analyzed to capture its 3-dimensional shape. It is also possible that the shape of the generic socket interior may be known from data developed/used in the manufacturing thereof. In such a case, capturing the shape of the generic socket interior is not necessary. A 3-dimensional electronic model of the generic socket interior can be optionally generated 110 for viewing by the user of the system. The 3-dimensional model of the residual limb may again be modified if desired 30, to assist in creating a liner of proper fit. Once any adjustments to the optional 3-dimensional model of the residual limb have been completed by the practitioner, the modelling software uses the data associated with both the residual limb shape and the interior of the generic prosthetic socket to globally and/or locally calculate the thickness of the liner 115 as required to ensure that its exterior will properly fit within the preselected generic prosthetic socket when the liner-covered residual limb is inserted therein. Once the liner thickness is calculated, a 3-dimensional electronic model of the liner is preferably displayed for viewing by the user of the system 120. As in the aforementioned embodiment, the user may be able to specify liner parameters and select options and/or accessories to be installed to/in the liner. As described in more detail above, the liner data is then sent to a manufacturing facility 25 for use in molding the custom prosthetic liner 75. It is contemplated that the generic prosthetic socket may be selected automatically by the modelling software based on the captured shape/size of the residual limb, may be specified by the practitioner, or may be selected from a database of generic sockets available as part of the aforementioned optional medical device configuring and purchasing system. The system and method of this embodiment of the present invention facilitates the construction of a prosthetic limb having a generic socket, while still providing a fit that is customized to an individual amputee. Hence, this embodiment of the system and method of the present invention permits the construction of a custom-fit prosthetic limb in less time, and at a reduced cost.

While certain embodiments of the present invention are described in detail above, the scope of the invention is not to be considered limited by such disclosure, and modifications are possible without departing from the spirit of the invention as evidenced by the following claims:

What is claimed is:

1. A method of producing a custom flexible polymeric prosthetic liner, comprising:

using a shape capture apparatus to capture the 3-dimensional shape of an amputee's residual limb;

providing a processing device in communication with said shape capture apparatus, said processing device for generating a 3-dimensional electronic model of said residual limb from said 3-dimensional shape captured by said shape capture apparatus:

providing a storage means in communication with said shape capture apparatus for temporarily storing data associated with said 3-dimensional shape of an amputee's residual limb:

providing a means of furnishing said data to a facility equipped to produce said custom prosthetic liner;

providing a means at said facility for associating prosthetic liner parameters with said data;

creating at least one custom mold component from said data associated with said 3-dimensional shape of an amputee's residual limb and said prosthetic liner parameters;

providing a mold for receiving and containing an amount of flexible polymeric material, said mold incorporating said at least one custom mold component; and using a molding machine to produce said custom prosthetic liner from said mold.

2. The method of claim 1, wherein said shape capture apparatus employs a plurality of spaced-apart image detectors.

3. The method of claim 1, wherein said storage means stores said data associated with the captured 3-dimensional shape of an amputee's residual limb on a machine readable medium for subsequent delivery to said facility equipped to produce said custom liner.

4. The method of claim 1, wherein said data associated with the captured 3-dimensional shape of an amputee's residual limb is remotely transmitted to said facility equipped to produce said custom liner.

5. The method of claim 1, wherein said data associated with the captured 3-dimensional shape of an amputee's residual limb is transmitted to said facility equipped to produce said custom liner over a local area network (LAN) or wireless local area network (WLAN).

6. The method of claim 1, wherein said processing device consists of a computer program in combination with a device selected from the group consisting of a laptop computer, a desktop computer, a pen computer, a pocket personal computer (pocket PC), and a personal data assistant (PDA).

7. The method of claim 1, further comprising a means for generating numerical data representative of said 3-dimensional model.

8. The method of claim 7, wherein said numerical data is generated after delivery of said data associated with the captured 3-dimensional shape of an amputee's residual limb to said facility equipped to produce said custom liner.

9. The method of claim 7, wherein said numerical data is generated by said shape capture apparatus or a device in communication with said shape capture apparatus, and said numerical data is subsequently provided to said facility equipped to produce said custom liner.

10. The method of claim 1, wherein said at least one custom mold component is produced by a computer-controlled machining device.

11. The method of claim 1, wherein said at least one custom mold component is created from a closed-cell foam material.

12. The method of claim 1, wherein said at least one custom mold component is a mold core for use with a common mold cavity.

13. The method of claim 12, wherein said mold cavity is selected based on its size.

14. The method of claim 1, wherein said at least one custom mold component is a mold cavity for use with a custom or common mold core.

15. The method of claim 1, wherein said custom prosthetic liner is manufactured from a silicone, urethane, or thermoplastic elastomer material.

16. The method of claim 15, wherein said custom prosthetic liner is manufactured from a block copolymer material.

17. The method of claim 1, wherein a fabric covering is applied to an outer surface of said custom prosthetic liner during the liner manufacturing process.

18. The method of claim 1, further comprising the ability to manipulate the data associated with said 3-dimensional shape of an amputee's residual limb to accommodate particular features of said residual limb in said custom prosthetic liner.

19. The method of claim 1, further comprising providing the ability to select liner materials and material properties.

20. The method of claim 1, further comprising providing the ability to specify accessories to be included in/on said custom prosthetic liner.

21. The method of claim 20, wherein the number, location, and orientation of said accessories may also be specified.

22. The method of claim 20, wherein said accessories are selected from the group consisting of suspension components, reinforcement, bladders (including inflatable bladders), additives, and sensors.

23. The method of claim 22, wherein said additives include antimicrobial substances.

24. The method of claim 1, further comprising a means of communication with an automated system for configuring and purchasing a medical device.

25. A system for producing a custom prosthetic liner that allows an amputee with a residual limb of changed shape and/or size to continue wearing an existing prosthetic socket, comprising:

a shape capture apparatus for capturing a 3-dimensional shape of said amputee's residual limb;

a shape capture apparatus for capturing a 3-dimensional shape of the interior of said existing prosthetic socket;

a processing device, said processing device running a computer program for generating a 3-dimensional electronic liner model by comparing the captured 3-dimensional shapes of said amputee's residual limb and said interior of said existing prosthetic socket, calculating a difference in size and/or shape between the outer surface of said residual limb and the interior surface of said existing prosthetic socket, and automatically adjusting the thickness of said liner model as needed to make up for said difference in size and/or shape;

an optional interface for allowing a user of said system to operate said computer program to view and modify a 3-dimensional electronic residual limb model if so desired;

a means of providing data associated with said 3-dimensional electronic liner model, said 3-dimensional electronic residual limb model, or both, to a manufacturing facility equipped to produce said custom prosthetic liner;

an apparatus for creating at least one custom mold component from said data; and a molding machine for producing said custom prosthetic liner from a mold incorporating said at least one custom mold component.

26. The system of claim 25, wherein said shape capture apparatus for capturing the 3-dimensional shape of said residual limb is also used to capture the 3-dimensional shape of the interior of said existing prosthetic socket.

27. The system of claim 25, wherein said processing device consists of a device selected from the group consisting of a laptop computer, a desktop computer, a pen computer, a pocket personal computer (pocket PC), and a personal data assistant (PDA).

28. The system of claim 25, wherein said data associated with said 3-dimensional electronic liner model, said 3-dimensional electronic residual limb model, or both, is provided to said manufacturing facility via the Internet.

29. The system of claim 25, wherein said data associated with said 3-dimensional electronic liner model, said 3-dimensional electronic residual limb model, or both, is transmitted to said manufacturing facility over a local area network (LAN) or wireless local area network (WLAN).

30. The system of claim 25, further comprising a storage means for temporarily storing data associated with the shape of said residual limb and said 3-dimensional electronic liner model.

31. The system of claim 30, wherein said storage means is selected from the group consisting of a hard disk, a floppy disk, a compact disc or other optical medium, a magneto-optical disk, a magnetic tape, and a PROM or similar other magnetic chip.

32. The system of claim 25, further comprising a transmission device for remotely transmitting said data associated with said 3-dimensional electronic liner model, said 3-dimensional electronic residual limb model, or both, to said manufacturing facility.

33. The system of claim 32, wherein said transmission device is selected from the group consisting of a dial-up modem, a DSL or ISDN modem, a cable modem, a WiFi card, a Bluetooth® card, a WCDMA card, a network interface card (NIC), or a wireless networking card.

34. The system of claim 25, wherein said at least one custom mold component is a mold core for use with a common mold cavity.

35. The system of claim 25, wherein said at least one custom mold component is a mold cavity for use with a custom or common mold core.

36. The system of claim 25, wherein said computer program also generates a viewable 3-dimensional electronic model of said existing prosthetic socket interior.

37. The system of claim 25, further comprising the ability to use said computer program to select liner materials and liner material properties.

38. The system of claim 25, further comprising the ability to use said computer program to specify accessories to be included in/on said custom prosthetic liner.

39. The system of claim 38, wherein the number, location, and orientation of said accessories may also be specified.

40. The system of claim 38, wherein said accessories are selected from the group consisting of suspension components, reinforcement, bladders (including inflatable bladders), additives, and sensors.

41. The system of claim 40, wherein said additives include antimicrobial substances.

42. The system of claim 25, wherein said custom prosthetic liner is manufactured from a silicone, urethane, or thermoplastic elastomer material.

43. The system of claim 42, wherein said custom prosthetic liner is manufactured from a block copolymer material.

44. A system for producing a custom prosthetic liner that allows the residual limb of an amputee to be custom fit to a generic prosthetic socket, comprising:
a shape capture apparatus for capturing the 3-dimensional shape of an amputee's residual limb;
socket data representative of the 3-dimensional shape of an interior of said a generic prosthetic socket;
a processing device, said processing device running a computer program for generating a 3-dimensional electronic liner model by comparing the captured 3-dimensional shape of said amputee's residual limb and said interior of said generic prosthetic socket, calculating a difference in size and/or shape between the outer surface of said residual limb and said interior surface of said generic prosthetic socket, and automatically adjusting the thickness of said liner model as needed to make up for said difference in size and/or shape;
an optional interface for allowing a user of said system to operate said computer program to view and modify a 3-dimensional electronic residual limb model if so desired;
a means of providing data associated with said 3-dimensional electronic liner model, said 3-dimensional electronic residual limb model, or both, to a manufacturing facility equipped to produce said custom prosthetic liner;
an apparatus for creating at least one custom mold component from said data; and
a molding machine for producing said custom prosthetic liner from a mold incorporating said at least one custom mold component.

45. The system of claim 44, wherein said socket data is available as a result of the socket manufacturing process.

46. The system of claim 44, wherein said socket data is obtained by capturing the 3-dimensional shape of the interior of said generic prosthetic socket.

47. The system of claim 44, wherein said shape capture apparatus for capturing the 3-dimensional shape of said residual limb is also used to capture the 3-dimensional shape of the interior of said generic prosthetic socket.

48. The system of claim 44, wherein said generic socket is preselected from a group of generic prosthetic sockets, based on its size.

49. The system of claim 44, wherein said processing device consists of a device selected from the group consisting of a laptop computer, a desktop computer, a pen computer, a pocket personal computer (pocket PC), and a personal data assistant (PDA).

50. The system of claim 44, wherein said data associated with said 3-dimensional electronic liner model, said 3-dimensional electronic residual limb model, or both, is provided to said manufacturing facility via the Internet.

51. The system of claim 44, wherein said data associated with said 3-dimensional electronic liner model, said 3-dimensional electronic residual limb model, or both, is transmitted to said manufacturing facility over a local area network (LAN) or wireless local area network (WLAN).

52. The system of claim 44, further comprising a storage means for temporarily storing data associated with the shape of said residual limb and said 3-dimensional electronic liner model.

53. The system of claim 44, wherein said storage means is selected from the group consisting of a hard disk, a floppy disk, a compact disc or other optical medium, a magneto-optical disk, a magnetic tape, and a PROM or similar other magnetic chip.

54. The system of claim 44, further comprising a transmission device for remotely transmitting said data associated with said 3-dimensional electronic liner model, said 3-dimensional electronic residual limb model, or both, to said manufacturing facility.

55. The system of claim 44, wherein said transmission device is selected from the group consisting of a dial-up modem, a DSL or ISDN modem, a cable modem, a WiFi card, a Bluetooth® card, a WCDMA card, a network interface card (Nb), or a wireless networking card.

56. The system of claim 44, wherein said at least one custom mold component is a mold core for use with a common mold cavity.

57. The system of claim 44, wherein said at least one custom mold component is a mold cavity for use with a custom or common mold core.

58. The system of claim 44, further comprising a separate system and computer program for facilitating the automatic configuration and purchasing of a medical device, said separate system and computer program accessible via said processing device.

59. The system of claim 58, wherein said generic socket may be selected from a database of said system and computer program for facilitating the automatic configuration and purchasing of a medical device.

60. The system of claim 44, wherein said computer program also generates a viewable 3-dimensional electronic model of said generic prosthetic socket interior.

61. The system of claim 44, further comprising the ability to use said computer program to select liner materials and liner material properties.

62. The system of claim 44, further comprising the ability to use said computer program to specify accessories to be included in/on said custom prosthetic liner.

63. The system of claim 62, wherein the number, location, and orientation of said accessories may also be specified.

64. The system of claim 62, wherein said accessories are selected from the group consisting of suspension components, reinforcement, bladders (including inflatable bladders), additives, and sensors.

65. The system of claim 64, wherein said additives include antimicrobial substances.

66. The system of claim 44, wherein said custom prosthetic liner is manufactured from a silicone, urethane, or thermoplastic elastomer material.

67. The system of claim 66, wherein said custom prosthetic liner is manufactured from a block copolymer material.

68. A method of producing a custom flexible polymeric prosthetic liner comprising:
- obtaining shape data associated with an amputee's residual limb;
- providing a processing device in conjunction with a computer program for generating a 3-dimensional electronic liner model from said shape data and liner parameters input by a user of said system;
- optionally, providing an interface for allowing a user of said system to operate said computer program to view and modify a 3-dimensional electronic residual limb model if so desired, data associated with said residual limb model subsequently used in generating said liner model;
- providing data associated with said residual limb shape, said 3-dimensional electronic liner model, or both, to a manufacturing facility equipped to produce said custom liner;
- creating at least one custom mold component from said data;
- providing a mold for receiving and containing an amount of flexible polymeric material, said mold incorporating said at least one custom mold component; and
- using a molding machine to produce said custom prosthetic liner from said mold;
- wherein said shape data is obtained from a cast of said residual limb.

69. The method of claim 68, wherein said shape data is obtained by first producing a cast of said residual limb.

70. The method of claim 69, further comprising electronically capturing a 3-dimensional image of an interior of said cast and providing electronic data associated therewith to said processing device.

71. The method of claim 70, wherein said image capturing is done at said manufacturing facility.

72. The method of claim 71, wherein said cast is sent to said manufacturing facility.

73. The method of claim 68, wherein said shape data is obtained by producing measurements of said residual limb.

74. The method of claim 73, further comprising entering said measurements into said system for use by said processing device.

75. The method of claim 68, wherein said processing device is selected from the group consisting of a laptop computer, a desktop computer, a pen computer, a pocket personal computer (pocket PC), and a personal data assistant (PDA).

76. The method of claim 68, wherein data associated with the shape of said residual limb, said 3-dimensional electronic liner model, or both, is stored on a machine readable medium and is manually delivered to said facility equipped to produce said custom liner.

77. The method of claim 68, wherein data associated with the shape of said residual limb, said 3-dimensional electronic liner model, or both, is remotely transmitted to said facility equipped to produce said custom liner.

78. The method of claim 68, wherein data associated with the shape of said residual limb, said 3-dimensional electronic liner model, or both, is transmitted to said facility equipped to produce said custom liner over a local area network (LAN) or wireless local area network (WLAN).

79. The method of claim 68, wherein said at least one custom mold component is produced from said data.

80. The method of claim 68, wherein said at least one custom mold component is created from a closed-cell foam material.

81. The method of claim 68, wherein said at least one custom mold component is a mold core for use with a common mold cavity.

82. The method of claim 81, wherein said mold cavity is selected based on its size.

83. The method of claim 68, wherein said at least one custom mold component is a mold cavity for use with a custom or common mold core.

84. The method of claim 68, wherein said custom prosthetic liner is manufactured from a silicone, urethane, or thermoplastic elastomer material.

85. The method of claim 84, wherein said custom prosthetic liner is manufactured from a block copolymer material.

86. The method of claim 68, wherein a fabric covering is applied to an outer surface of said custom prosthetic liner during the liner manufacturing process.

87. The method of claim 68, further comprising the ability to select liner materials and liner material properties.

88. The method of claim 68, further comprising the ability to specify accessories to be included in/on said custom prosthetic liner.

89. The method of claim 88, wherein the number, location, and orientation of said accessories may also be specified.

90. The method of claim 88, wherein said accessories are selected from the group consisting of suspension components, reinforcement, bladders (including inflatable bladders), additives, and sensors.

91. The method of claim 90, wherein said additives include antimicrobial substances.

92. The method of claim 68, further comprising a means of communication with an automated system for configuring and purchasing a medical device.

* * * * *

UNITED STATES PATENT AND TRADEMARK OFFICE
CERTIFICATE OF CORRECTION

PATENT NO. : 7,162,322 B2  
APPLICATION NO. : 10/724526  
DATED : January 9, 2007  
INVENTOR(S) : Robert E. Arbogast et al.

Page 1 of 1

It is certified that error appears in the above-identified patent and that said Letters Patent is hereby corrected as shown below:

In column 4, line 41, please delete "Alphas " and insert --Alpha® --.

In column 19, claim 44, line 7, please delete "said".

In column 20, claim 55, line 5, please delete "(Nb)" and insert --(NIC) --.

Signed and Sealed this

Thirteenth Day of March, 2007

JON W. DUDAS  
*Director of the United States Patent and Trademark Office*